United States Patent [19]

LaRochelle et al.

[11] 3,965,134

[45] June 22, 1976

[54] PROCESS FOR MAKING SILARYLENESILANEDIOL

[75] Inventors: Ronald W. LaRochelle, Schenectady; Tyrone D. Mitchell, Troy, both of N.Y.

[73] Assignee: General Electric Company, Schenectady, N.Y.

[22] Filed: Oct. 10, 1975

[21] Appl. No.: 621,527

[52] U.S. Cl. .................. 260/448.2 E; 260/448.2 D
[51] Int. Cl.$^2$ ............................................ C07F 7/08
[58] Field of Search ............................ 260/448.2 E

[56] References Cited
UNITED STATES PATENTS 3,209,018  9/1965  Merker .................. 260/46.5 R
3,338,870  8/1967  Nitzsche et al. .......... 260/448.2 E X Primary Examiner—Paul F. Shaver
Attorney, Agent, or Firm—William A. Teoli; Joseph T. Cohen; Jerome C. Squillaro

[57] ABSTRACT

A method is provided for making silarylenesilanediol. An aqueous mixture of a dialkoxy silarylene and a water miscible organic solvent, such as acetone, is refluxed. Water is combined with the resulting mixture to effect the separation of silarylenesilanediol which can be used to make polysilarylenesiloxanes.

5 Claims, No Drawings

PROCESS FOR MAKING SILARYLENESILANEDIOL

A method is provided for making silarylenesilanediol from dialkoxysilarylene in an aqueous water miscible organic solvent mixture.

Prior to the present invention, one method for making silarylenesilanediol was to treat various silarylenesilane compounds of the formula

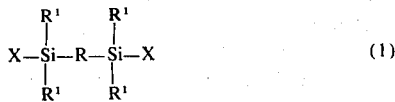

where X is a radical selected from halogen, $C_{(1-8)}$ alkoxy and hydrogen, R is a divalent aromatic organic radical, and $R^1$ is a monovalent organic radical with sodium hydroxide or potassium hydroxide in alcohol and water. Inasmuch as up to two moles or more of alkali hydroxide, per mole of the silarylenesilane of formula (1) were required, neutralization of the mixture had to be resorted to before silarylenesilanediol was isolated. A typical procedure used to make silarylenesilanediol from silarylenesilane dihydride by the strong base method is shown by Merker U.S. Pat. No. 3,202,634 in column 6, lines 1–25. Another strong base procedure which can be used to produce silarylenesilanediol involves the use of m-phenylene bis(dimethylethoxysilane), as shown by L. W. Breed et al in the J. Organometal Chem. 9 (1967), on page 191. In addition to requiring neutralization of the base before the silarylenesilanediol can be isolated, a purification strip is often required to eliminate salts from the mixture. As a result, the strong base technique for making silarylenesilanediol is undesirable in many respects.

Another procedure for making silarylenesilanediol as taught in copending application Ser. No. 563,785, filed 3/31/75 of R. W. LaRochelle, assigned to the same assignee as the present invention, is by refluxing an aqueous mixture of water miscible organic solvent and a dialkoxy silarylene of the formula,

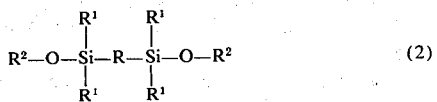

at temperatures of about 0°C to 100°C were R and $R^1$ are as previously defined, and $R^2$ is a $C_{(1-8)}$ alkyl radical followed by stripping the mixture of volatiles. Neutralization of strong base, and isolation and removal of undesirable salt byproducts from the resulting silanol-terminated silarylenesiloxane is not required. However, the stripping of the mixture to recover the silarylenesilanediol can lead to oligomerization and higher molecular weight silanol terminated silarylenesiloxane reaction products.

It would be desirable to be able to make silarylenesilanediol without the use of strong base procedures resulting in oligomerization to overcome the problems discussed above. The present invention is based on the discovery that the above described procedure involving refluxing the dialkoxysilarylene of formula (2) in an aqueous water miscible organic solvent mixture does not have to be stripped of volatiles to effect recovery of silarylenesilanediol. Separation of substantially pure silarylenesilanediol can be achieved by combining the reflux mixture with excess water. As a result, opportunities for oligomerization during stripping are eliminated.

There is provided by the present invention, a silarylenesilanediol which comprises, 1. refluxing a liquid phase mixture containing as essential ingredients, dialkoxysilarylene, of formula (2), water, and a water miscible organic solvent, and
2. combining the mixture of (1) with at least 2 parts of water per part of water miscible organic solvent used in the mixture of (1), and
3. recovering silarylenesilanediol from (2).

Included by the dialkoxysilarylene of formula (2) are, for example,

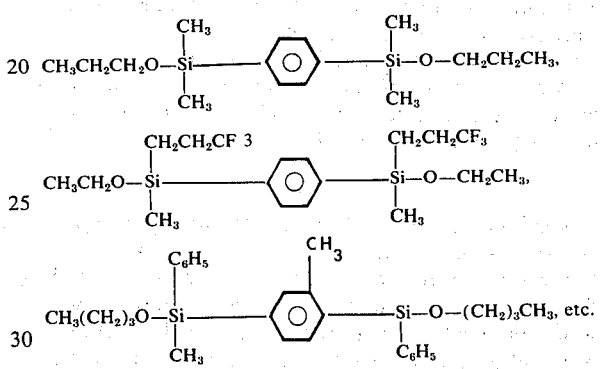

Radicals included by R of formula (2), for example, divalent aromatic hydrocarbon radicals, such as phenylene, tolylene, xylylene, naphthalene, 4,4'-biphenylene, 4,4'-diphenylene ether, etc.; halogenated divalent aromatic hydrocarbon radicals, such as chlorophenylene, bromonaphthalene, etc. Included by the monovalent organic radicals ($R^1$) of formula (2) are, for example, alkyl radicals, such as methyl, ethyl and propyl; aryl radicals, such as phenyl and naphthyl; alkaryl radicals, such as tolyl and xylyl; unsaturated aliphatic radicals, such as vinyl, allyl, propynyl; and halogenated radicals, such as chlorophenyl and 3,3,3-trifluoropropyl. Included by the $R^2$ radicals of formula (2) are, for example, $C_{1-8}$ alkyl radicals, such as methyl, ethyl, propyl, butyl, etc. In formula (2), where R and $R^1$ can be more than one radical respectively, these radicals can be the same or different as previously defined.

In the practice of the invention, a mixture of dialkoxysilarylene, water and water miscible solvent, is refluxed to effect the hydrolysis of the dialkoxysilarylene to silarylenesilanediol or diol. There is then added additional water to the reflux mixture to effect separation of silarylenesilanediol.

In making the silarylenesilanediol there can be employed from 0.5 to 10 parts of water miscible organic solvent, per part of the dialkoxysilarylene. Sufficient water can be used to provide at least two moles of water per mole of the dialkoxysilarylene with an upper amount of water being limited only by economic considerations. Agitation, such as stirring, will facilitate hydrolysis. Suitable water miscible organic solvents, which can be used during reflux are, for example, acetone, acetonitrile, tetrahydrofuran, dioxane, methylethyl ketone, etc.

After the mixture has been refluxed over a period of about 2 hours or more additional water can be added to provide at least two parts of water per part of water miscible organic solvent while 2 to 5 parts of water are preferred. However, 2 to 20 parts or higher, per part of water miscible organic solvent, will effectively provide separation of the diol. The diol can be recovered from the mixture by standard filtration, decantation, or centrifugation means. The diol thereafter can be heated with a solvent, such as toluene, to azeotrope out the last traces of water.

The silarylenesilanediol, which is made by the method of the present invention, can be used to make silarylenesiloxane polymers, as shown in Merker U.S. Pat. No. 3,202,634. In addition, the silarylenesilanediol can be used to make silarylenesiloxane containing block copolymers, such as shown in copending application Ser. No. 563,785, of Ronald W. LaRochelle et al., assigned to the same assignee as the present invention which contain a critical mole percent range of chemically combined organoalkenylsiloxy units.

In order that those skilled in the art will be better able to practice the invention, the following examples are given by way of illustration and not by way of limitation. All parts are by weight.

EXAMPLE 1

A solution of 31 parts of p-bis(dimethyl-n-propoxysilyl)benzene, 15 parts of water and 100 parts of acetonitrile was refluxed for 20 hours. There was added 500 parts of water to the resulting mixture. A white solid immediately separated. Based on the method of preparation the white solid was p-bis(dimethylhydroxysilyl)benzene, which was recovered by filtration. It was then recrystallized from hot toluene. There was obtained a 86% yield of product having a melting point of 134°–135°C. This confirmed the identity of the product as being p-bis(dimethylhydroxysilyl)benzene which is reported by Merker U.S. Pat. No. 3,202,634 to have a melting point of 136°–137°C.

EXAMPLE 2

A solution of 3 parts of p-bis(dimethyl-n-propoxysilyl)benzene, 1.5 parts of water and 10 parts of acetone was refluxed for 48 hours. There was then added to the mixture 50 parts of water resulting in the percipitation of a white solid. The solid was isolated and recrystallized as described in Example 1. There was obtained a nearly quantitative yield of product having a melting point of 133°–135°C which established its identity as p-bis(dimethylhydroxysilyl)benzene.

EXAMPLE 3

There was added 30 parts of an α,ω-dihydroxypolydimethylsiloxane fluid having a viscosity of 62 centistokes, 25 parts of toluene, and 0.5 parts of tetramethylguanidine di-2-ethylhexoate to 22 parts of p-bis(dimethylhydroxysilyl)benzene prepared in accordance with Example 1. The mixture was refluxed for 6.5 hours at 110°C. There was obtained a viscous polymer which was dissolved in chloroform and precipitated into methanol. The polymer was isolated by decantation and dried at 75°C at 35 torr. There was obtained a block polymer having an average silphenylenesiloxane block length of at least 9 units in the silphenylene block and an average of at least 36 dimethylsiloxy units in the polydimethylsiloxane block. The intrinsic viscosity of the block polymer was 0.644 dl/g in toluene at 25°C.

Although the above examples are limited to only a few of the very many variations which can be used in the practice of the method of the present invention, such as various dialkoxy silarylene of formula 2, other types of water miscible organic solvents, etc., it should be understood that the method of the present invention is broadly directed to making silarylenesilanediol by refluxng an aqueous water miscible organic solvent mixture of dialkoxysilarylene of formula 2 where the other parameters are shown in the description preceding these examples.

What we claim as new and desire to secure by Letters of Patent of the United States is:

1. In a method for making silarylenesilanediol comprising the steps of
    1. refluxing a mixture consisting essentially of a dialkoxy silarylene, water and water miscible organic solvent and
    2. stripping the mixture of volatiles under reduced pressure to a temperature of about 100°C to produce a product consistng essentially of silanol-terminated silarylene-siloxane, the improvement which comprises, combining the mixture of (1) with at least 2 parts of water per part of water miscible organic solvent used in the mixture, to effect the separation of silarylenesilanediol from the resulting mixture, whereby step (2) involving the stripping of the mixture of (1) is eliminated.

2. A method in accordance with claim 1, where the dialkoxysilarylene is dialkoxysilphenylene.

3. A method in accordance with claim 1, where the dialkoxysilarylene is p-bis(dimethyl-n-propoxysilyl)benzene.

4. A method in accordance with claim 1, where the water miscible organic solvent is acetonitrile.

5. A method in accordance with claim 1, where the water miscible organic solvent is acetone.

* * * * *